(12) United States Patent
Flow

(10) Patent No.: US 10,499,731 B2
(45) Date of Patent: Dec. 10, 2019

(54) APPARATUS FOR SORTING OF CROP COMPONENTS

(71) Applicant: THE FLOWR CANNABIS ULC, Markham (CA)

(72) Inventor: Thomas Flow, Kelowna (CA)

(*) Notice: Subject to any disclaimer, the term of this patent is extended or adjusted under 35 U.S.C. 154(b) by 0 days.

(21) Appl. No.: 15/912,356

(22) Filed: Mar. 5, 2018

(65) Prior Publication Data

US 2019/0269238 A1 Sep. 5, 2019

(51) Int. Cl.
| | |
|---|---|
| *A47B 13/08* | (2006.01) |
| *A61K 36/185* | (2006.01) |
| *B07B 13/00* | (2006.01) |
| *A61K 31/352* | (2006.01) |

(52) U.S. Cl.
CPC ............ *A47B 13/08* (2013.01); *A61K 31/352* (2013.01); *A61K 36/185* (2013.01); *B07B 13/003* (2013.01); *A47B 2200/0001* (2013.01)

(58) Field of Classification Search
CPC ............ A47B 13/08; A47B 2200/0001; A47B 2200/0042; A47B 2200/0046; A47B 2009/003; A47B 2021/0364; A47B 37/00; A47B 2200/03; A61K 31/352; A61K 36/185; B07B 13/003; Y10S 209/911; B65B 39/00
USPC .............................................. 108/161, 24, 25
See application file for complete search history.

(56) References Cited

U.S. PATENT DOCUMENTS

| | | | |
|---|---|---|---|
| 612,759 A | * | 10/1898 | Wartman |
| 646,218 A | | 3/1900 | Hollingsworth |
| 948,954 A | | 2/1910 | Cody et al. |
| 1,411,684 A | | 4/1922 | Debney |
| 1,452,494 A | | 4/1923 | Dalitz |
| 1,535,761 A | | 4/1925 | Boyles |
| 1,568,154 A | * | 1/1926 | Hannon ................ A47B 25/00 108/26 |
| 1,763,174 A | | 6/1930 | Morris |
| 2,457,038 A | | 12/1948 | Garonis |
| 2,478,374 A | | 8/1949 | Danielson |
| 3,083,517 A | | 4/1963 | Wilson |
| 3,160,482 A | | 12/1964 | Foote |
| 3,193,970 A | | 7/1965 | Green |

(Continued)

FOREIGN PATENT DOCUMENTS

| | | |
|---|---|---|
| CA | 2155859 | 8/1994 |
| CA | 2232747 | 10/1998 |

(Continued)

OTHER PUBLICATIONS

CN 203902118; abstract and figure; Han et al (Year: 2014).*

(Continued)

*Primary Examiner* — Janet M Wilkens
(74) *Attorney, Agent, or Firm* — Richard D. Okimaw

(57) ABSTRACT

An apparatus for sorting crop components comprises a tabletop having a top and a bottom surface and an outer edge therearound, an inner edge spaced inwards and apart from the outer edge of the tabletop and a lower surface parallel to and spaced apart from the tabletop. The apparatus further comprises at least two spaced apart apertures extending through the lower surface with angled walls extending down from the inner edge to the lower surface and a plurality of vertical table legs supporting the tabletop.

7 Claims, 2 Drawing Sheets

(56) References Cited

U.S. PATENT DOCUMENTS

| | | | |
|---|---|---|---|
| 3,659,889 A | 5/1972 | Whitley | |
| 3,935,959 A | 2/1976 | Long | |
| 3,999,303 A | 12/1976 | Martin et al. | |
| 4,033,461 A | 7/1977 | Nevai | |
| 4,280,780 A | 7/1981 | Neufeldt | |
| 4,335,540 A | 6/1982 | Allen | |
| 4,520,579 A | 6/1985 | De Cloet et al. | |
| 4,653,737 A | 3/1987 | Haskins et al. | |
| 4,747,352 A | 5/1988 | Guidry et al. | |
| D306,100 S * | 2/1990 | Wende | 108/24 |
| 5,109,990 A | 5/1992 | Murphy et al. | |
| 5,212,905 A | 5/1993 | Philoctete | |
| 5,226,621 A | 7/1993 | Skoff | |
| 5,363,755 A | 11/1994 | Liang | |
| 5,572,934 A * | 11/1996 | Aldridge | A47B 3/0912 108/24 |
| 6,070,359 A | 6/2000 | Liu | |
| 6,105,640 A | 8/2000 | Holand et al. | |
| 6,321,662 B1 * | 11/2001 | Fraise | A47B 37/00 108/25 |
| 6,341,704 B1 | 1/2002 | Michel, Jr. | |
| 6,810,819 B2 | 11/2004 | Kaniuk et al. | |
| 6,846,177 B1 | 1/2005 | Hutchens | |
| 7,080,484 B2 | 7/2006 | Littge | |
| 7,122,119 B2 | 10/2006 | Gribble et al. | |
| 7,832,146 B2 | 11/2010 | Gordon | |
| 8,104,152 B2 * | 1/2012 | Spiers | A61G 17/00 27/19 |
| 8,642,910 B2 | 2/2014 | Pellenc et al. | |
| 8,800,202 B2 | 8/2014 | Rusiniak | |
| 8,863,947 B2 | 10/2014 | Sibley | |
| 9,032,567 B1 | 5/2015 | Galgano | |
| 9,301,462 B2 | 4/2016 | Azoulay | |
| 9,371,470 B2 | 6/2016 | Ward | |
| 9,462,757 B2 | 10/2016 | Rusiniak | |
| 9,565,812 B2 | 2/2017 | Wilson | |
| 9,574,333 B2 | 2/2017 | O'Brien et al. | |
| D831,395 S * | 10/2018 | Vargas, II | D6/707.19 |
| 2005/0155286 A1 | 4/2005 | Soukup | |
| 2005/0109245 A1 * | 5/2005 | Pote | A47B 37/00 108/25 |
| 2006/0076744 A1 | 4/2006 | Martin | |
| 2006/0242895 A1 | 11/2006 | Winkler | |
| 2009/0056595 A1 * | 3/2009 | Dean | A47B 3/0911 108/24 |
| 2013/0086742 A1 | 4/2013 | Didehvar et al. | |
| 2013/0283521 A1 | 10/2013 | Jain et al. | |
| 2013/0326950 A1 | 12/2013 | Nilles | |
| 2014/0325909 A1 | 11/2014 | Faris | |
| 2015/0027096 A1 | 1/2015 | Black et al. | |
| 2015/0033606 A1 * | 2/2015 | Dinlocker | A47G 1/14 40/727 |
| 2015/0075129 A1 | 3/2015 | Mooneyhan | |
| 2015/0096189 A1 | 4/2015 | Hawes et al. | |
| 2016/0066519 A1 | 3/2016 | Jansen | |
| 2016/0107796 A1 | 4/2016 | Sibley | |
| 2016/0363310 A1 * | 12/2016 | Powell | F21V 33/0012 |
| 2017/0071143 A1 | 3/2017 | Newsam | |
| 2017/0094920 A1 | 4/2017 | Ellins et al. | |
| 2017/0112181 A1 | 4/2017 | Belfance et al. | |
| 2017/0265408 A1 | 9/2017 | McGowan et al. | |

FOREIGN PATENT DOCUMENTS

| | | |
|---|---|---|
| CA | 2794910 | 11/2013 |
| CA | 2886532 | 9/2015 |
| CN | 102334741 | 1/2012 |
| CN | 204165341 | 10/2014 |
| CN | 204630272 | 9/2015 |
| CN | 205968910 | 2/2017 |
| CN | 206525538 | 9/2017 |
| EP | 666043 | 7/1991 |
| EP | 1332666 | 12/2006 |
| EP | 2071979 | 12/2007 |
| FR | 2942977 | * 9/2010 |
| GB | 2398369 | 2/2003 |
| GB | 2505914 | 3/2014 |
| GB | 2509717 | 7/2014 |
| WO | 200504687 | 1/2005 |
| WO | 201634719 | 3/2016 |
| WO | 201727813 | 2/2017 |

OTHER PUBLICATIONS

Architectural Salvage Sluice Sink, 1 Page, www.arcsal.com Sluice Sink—NPL.

International Searching Authority, The International Search Report and the Written Opinion of the International Searching Authority, or the Declaration, International Application No. PCT/CA2019/050266, Filed Mar. 5, 2019, 8 pages, Receiving Office—Canadian Intellectual Property Office.

* cited by examiner

APPARATUS FOR SORTING OF CROP COMPONENTS

BACKGROUND OF THE INVENTION

1. Field of Invention

The present invention relates generally to an apparatus for sorting of crop components, and in particular to a trimming table for use when trimming *cannabis* plants.

2. Description of Related Art

The *cannabis* plant naturally includes both usable and unusable, or disposable, components. When harvesting a *cannabis* crop, the unusable components, such as the large fan leaves and stems, are discarded. Smaller "sugar leaves" may be retained to be processed into usable products, such as edibles, extracts or hash. Finally, the colas are retained separately from the sugar leaves, and may be dried or used to make extractions.

Typically, when trimming a *cannabis* plant, a variety of containers are used to separate the disposable components from the sugar leaves and colas. The use of several containers can be cumbersome for the user.

SUMMARY OF THE INVENTION

According to a first embodiment of the present invention there is disclosed an apparatus for sorting crop components comprising a tabletop having a top and a bottom surface and an outer edge therearound, an inner edge spaced inwards and apart from the outer edge of the tabletop and a lower surface parallel to and spaced apart from the tabletop. The apparatus further comprises at least two spaced apart apertures extending through the lower surface with angled walls extending down from the inner edge to the lower surface and a plurality of vertical table legs supporting the tabletop.

The tabletop may be formed in a generally rectangular configuration. The inner edge may spaced apart from the outer edge by a distance in the range of 2 to 12 inches. The lower surface may be spaced apart from the tabletop by a distance in the range of 4 to 12 inches. The angled walls may be oriented at an angle of between 30 degrees and 60 degrees relative to vertical. The plurality of vertical table legs may include rollers on a bottom distal end thereof.

The apparatus may further comprise vertical walls extending down from the lower surface around the apertures.

Other aspects and features of the present invention will become apparent to those ordinarily skilled in the art upon review of the following description of specific embodiments of the invention in conjunction with the accompanying figures.

BRIEF DESCRIPTION OF THE DRAWINGS

In drawings which illustrate embodiments of the invention wherein similar characters of reference denote corresponding parts in each view.

DETAILED DESCRIPTION

Figure 1:
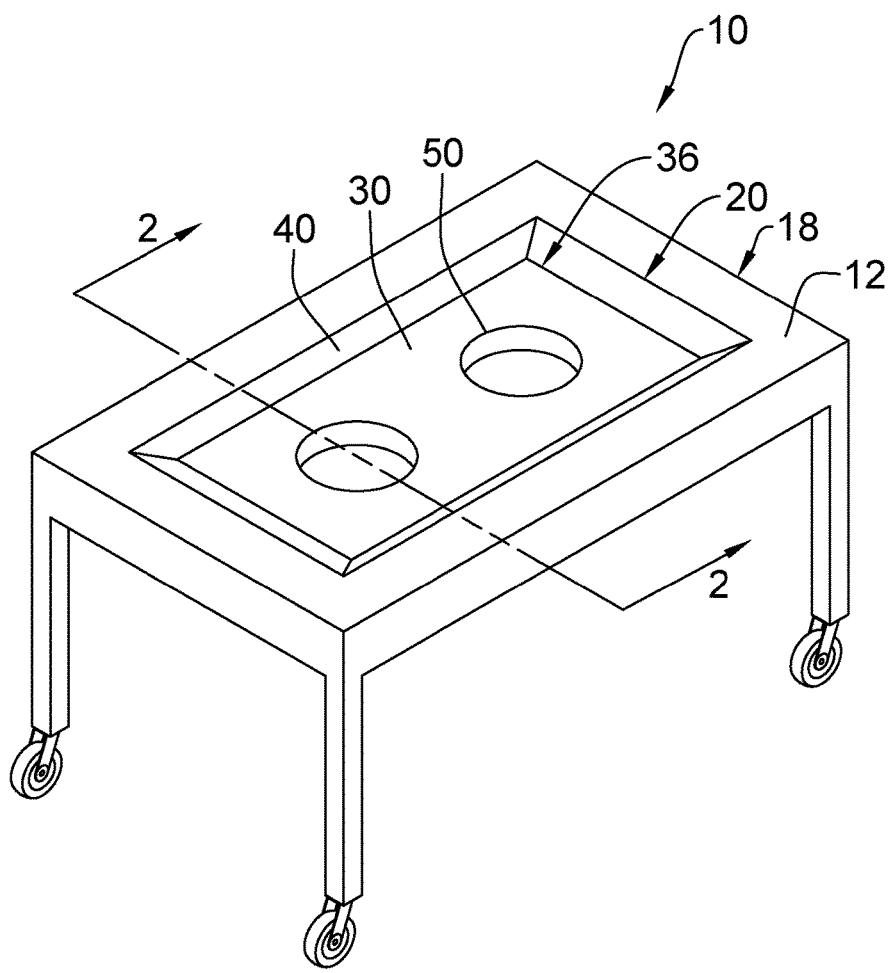
FIG. 1 is a perspective view of an apparatus for sorting crop components according to a first embodiment of the invention.

Referring to FIG. 1, an apparatus for sorting crop components according to a first embodiment of the invention is shown generally at 10. The apparatus 10 includes a horizontal tabletop 12 supported by a plurality of vertical table legs 60. An inner lower surface 30 is vertically spaced apart below the tabletop 12 with angled walls 40 therebetween. At least two spaced apart apertures 50 extend through the lower surface 30, providing access to sorting or disposal containers (not shown) therebelow.

Figure 2:
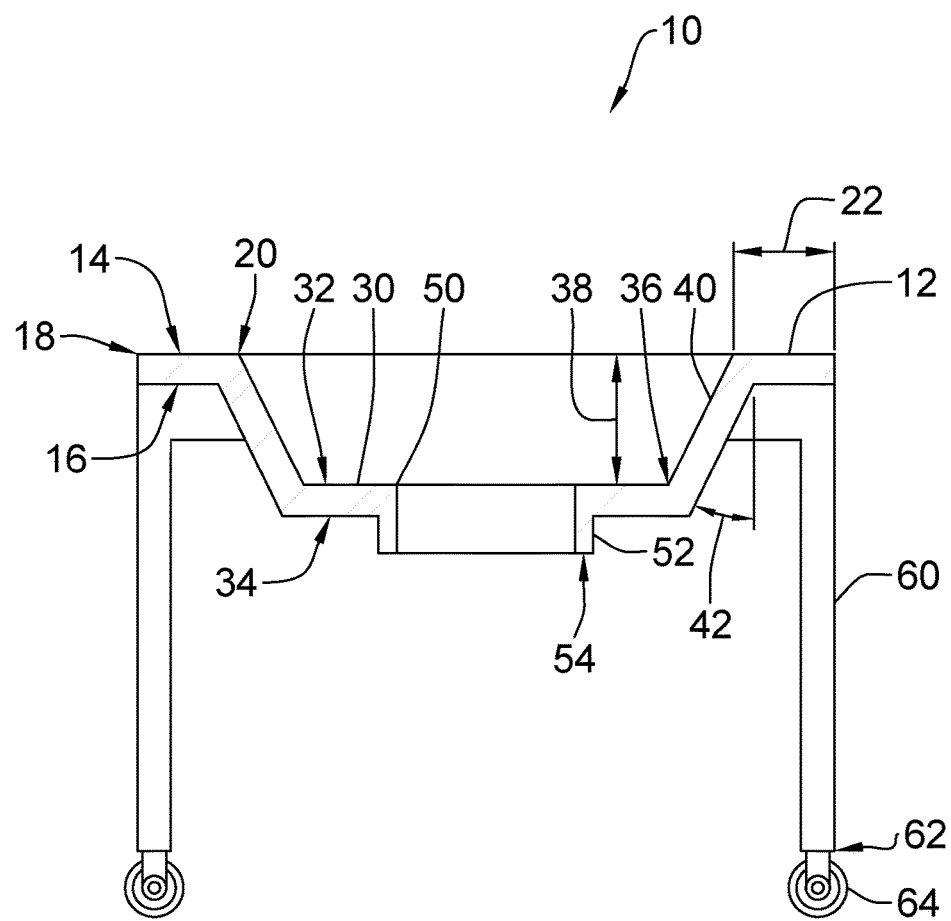
FIG. 2 is a cross-sectional view of the apparatus of FIG. 1 taken along the line 2-2.

Referring to FIGS. 1 and 2, the tabletop 12 includes top and bottom surfaces 14 and 16, respectively, with an outer edge 18 extending therearound. An inner edge 20 is spaced apart from the outer edge 18 by a distance 22 in the range of such as, by way of non-limiting example, 2 to 12 inches (5 cm to 30 cm).

The lower surface 30 includes top and bottom surfaces 32 and 34, respectively, with an outer edge 36 extending therearound. The angled walls 40 extend down from the inner edge 20 to the outer edge 36 at an angle 42 such as, by way of non-limiting example, in the range of 30 to 60 degrees from vertical. The lower surface 30 is spaced apart from the tabletop 12 by a vertical distance 38 in the range of such as, by way of non-limiting example, 4 to 12 inches (10 cm to 30 cm).

The apertures 50 are spaced apart from the outer edge 36 and extend through the top and bottom surfaces, 32 and 34, of the lower surface 30. Each aperture 50 includes a vertical wall 52 therearound extending from the bottom surface 34 of the lower surface 30 to a bottom edge 54. As illustrated, the vertical wall 52 may be cylindrical, although it will be appreciated that the vertical wall may be in any shape to correspond with each aperture 50.

The plurality of table legs 60 extend from the tabletop 12 to a bottom distal end 62. Rollers 64 are secured to the bottom distal end 62, as is commonly known, to facilitate movement of the apparatus.

When trimming a *cannabis* crop, containers are placed below the apertures 50 to collect the usable and unusable portions of the plant. A user may retain the usable portions in a container through one aperture 50, and dispose of the usable portions into another container through the second aperture 50. The trimmed plant may then be hung to dry.

While specific embodiments of the invention have been described and illustrated, such embodiments should be considered illustrative of the invention only and not as limiting the invention as construed in accordance with the accompanying claims.

What is claimed is:

1. An apparatus for sorting crop components comprising:
   a tabletop having a top and a bottom surface and an outer edge therearound;
   an inner edge spaced inwards and apart from said outer edge of said tabletop,
   wherein said tabletop forms a solid, one-piece, flat, unobstructed working surface extending from said outer edge to said inner edge;
   a lower surface parallel to and spaced below said tabletop;
   at least two spaced apart apertures extending through said lower surface;
   angled walls extending down from said inner edge to said lower surface,
   wherein said lower surface forms a substantially flat unobstructed working surface between said angled walls and said at least two spaced apart apertures; and
   a plurality of vertical table legs supporting said tabletop.
2. The apparatus of claim 1 wherein said tabletop is formed in a generally rectangular configuration.

3. The apparatus of claim 1 wherein said inner edge is spaced apart from said outer edge by a distance in the range of 2 to 12 inches.

4. The apparatus of claim 1 wherein said lower surface is spaced apart from said tabletop by a distance in the range of 4 to 12 inches.

5. The apparatus of claim 1 wherein said angled walls are oriented at an angle of between 30 degrees and 60 degrees relative to vertical.

6. The apparatus of claim 1 wherein said plurality of vertical table legs include rollers on a bottom distal end thereof.

7. The apparatus of claim 1 further comprising vertical walls extending down from said lower surface around said apertures.

\* \* \* \* \*